(12) United States Patent
Dobbins et al.

(10) Patent No.: US 6,369,200 B2
(45) Date of Patent: Apr. 9, 2002

(54) SOY ISOFLAVONE CONCENTRATE PROCESS AND PRODUCT

(75) Inventors: Thomas A. Dobbins, Howard, OH (US); Arthur H. Konwinski, Fort Wayne, IN (US)

(73) Assignee: Central Soya Company, Inc., Fort Wayne, IN (US)

( * ) Notice: Subject to any disclaimer, the term of this patent is extended or adjusted under 35 U.S.C. 154(b) by 0 days.

(21) Appl. No.: 09/730,000

(22) Filed: Dec. 4, 2000

Related U.S. Application Data

(63) Continuation-in-part of application No. 09/169,896, filed on Oct. 12, 1998, now Pat. No. 6,228,993.
(60) Provisional application No. 60/062,046, filed on Oct. 15, 1997.

(51) Int. Cl.[7] .............................. A23J 1/14; A23J 1/09; A23L 1/20; A23L 1/28; C07D 311/04
(52) U.S. Cl. ....................... 530/378; 426/634; 426/429; 426/431; 426/490; 426/520; 549/403
(58) Field of Search ................................ 426/634, 429, 426/431, 490, 520; 549/403; 530/378

(56) References Cited

U.S. PATENT DOCUMENTS

| | | | |
|---|---|---|---|
| 3,870,805 A | 3/1975 | Hayes et al. | 426/656 |
| 4,264,509 A | 4/1981 | Zilliken | 260/345.2 |
| 4,366,082 A | 12/1982 | Zilliken | 435/125 |
| 4,390,559 A | 6/1983 | Zilliken | 426/545 |
| 4,428,876 A | 1/1984 | Zilliken | 260/123.5 |
| 5,141,746 A | 8/1992 | Fleury et al. | 424/195.1 |
| 5,320,449 A | 6/1994 | Shen et al. | 435/68.1 |
| 5,352,384 A | 10/1994 | Shen et al. | 252/398 |
| 5,637,562 A | 6/1997 | Shen et al. | 514/2 |
| 5,670,632 A | 9/1997 | Chaihorsky | 536/8 |
| 5,679,806 A | 10/1997 | Zheng | 549/403 |
| 5,702,752 A | 12/1997 | Gugger et al. | 426/634 |
| 5,726,034 A | 3/1998 | Bryan et al. | 435/68.1 |
| 5,763,389 A | 6/1998 | Shen et al. | 514/2 |
| 5,792,503 A | 8/1998 | Gugger et al. | 426/634 |
| 5,821,361 A | 10/1998 | Waggle et al. | 436/128 |
| 5,827,682 A | 10/1998 | Bryan et al. | 435/68.1 |
| 5,851,792 A | 12/1998 | Shen et al. | 435/68.1 |
| 5,855,892 A | 1/1999 | Potter et al. | 424/757 |
| 5,858,449 A | 1/1999 | Crank et al. | 426/556 |
| 5,919,921 A | 7/1999 | Waggle et al. | 536/128 |
| 5,932,221 A | 8/1999 | Day | 424/195.1 |
| 5,936,069 A | 8/1999 | Johnson et al. | 530/370 |
| 5,952,374 A | 9/1999 | Clarkson, Jr. et al. | 514/456 |
| 5,968,516 A | 10/1999 | Liu et al. | 424/195.1 |
| 5,990,291 A | 11/1999 | Waggle et al. | 536/8 |
| 5,994,508 A | 11/1999 | Bryan et al. | 530/378 |
| 6,013,771 A | 1/2000 | Shen et al. | 530/378 |
| 6,015,785 A | 1/2000 | Shen et al. | 514/2 |
| 6,020,471 A | 2/2000 | Johns | 536/8 |
| 6,033,714 A * | 3/2000 | Gugger et al. | 426/634 |
| 6,083,553 A | 7/2000 | Waggle et al. | 426/629 |
| 6,132,795 A | 10/2000 | Holbrook et al. | 426/634 |
| 6,140,469 A | 10/2000 | Shen et al. | 530/370 |
| 6,146,448 A | 11/2000 | Kelly et al. | 95/287 |
| 6,146,669 A | 11/2000 | Jones et al. | 426/53 |
| 6,159,715 A | 12/2000 | Porter et al. | 435/170 |
| 6,171,638 B1 | 1/2001 | Gugger et al. | 426/634 |

OTHER PUBLICATIONS

Isoflavones and Their Conjugates in Soy Foods: Extraction Conditions and Analysis by HPLC—Mass Spectrometry; Barnes, Stephen et al.: Agric. Food Chem.; vol. 42, No. 11, pp. 2466–2474 (1994).

The Phytoestrogens, Isoflavones, in Soybean Foods in the American and Asian Diets; Barnes, Stephen et al.; unpublished observations; reprints available from Dr. Stephen Barnes, Department of Pharmacology, University of Alabama at Birmingham; sent to Central Soya Company in Jul. 1991.

Genistein, Daidzein, and Their β–Glycoside Conjugates; Antitumor Isoflavones in Soybeans from American and Asian Diets; Coward, Lori et al.; J. Agric. Food Chem.; vol. 41, No. 11, pp. 1961–1967 (1993).

CRC Critical Reviews in Food Science and Nutrition; vol. 27, Issue 4, p. 230 (1988).

Determination of Isoflavones in Soybean Flours, Proteins, Concentrates, and Isolates; Eldridge, Arthur C.: J. Agric. Food Chem.; vol. 30, No. 2, pp. 353–355 (1982).

Malonyl Isoflavone Glycosides in Soybean Seeds (Glycine max Merrill); Kudou, Shigemitsu et al.; Agric. Biol. Chem.; 55(9), 2227–2233 (1991).

Mass Balance Study of Isoflavones during Soybean Processing; Murphy, Patricia A.: J. Agric. Food Chem.; vol. 44, No. 8, pp. 2377–2383 (1996).

Genistin (an Isoflavone Glucoside) and Its Aglucone, Genistein, from Soybeans; Walter, E.D.; The Journal of American Chemical Society; vol. 63, pp. 3273–3276 (Dec. 1941).

Isoflavone and saponin glucosides in Soy hispida; Walz, E.; Annalen der Chemie; vol. 489, pp. 118–155; (1931?) (Note: includes English translation from German).

* cited by examiner

Primary Examiner—Jezia Riley
(74) Attorney, Agent, or Firm—Michael L. Fuelling

(57) ABSTRACT

A novel process for making an isoflavone concentrate product from soybeans which includes diluting solubles from alcohol-extracted hexane-defatted soybean flakes to about 10% to about 30% solids, separating undissolved solids from the diluted soy solubles, such that the separated solids have at least 4% isoflavones by weight of dry matter. That concentrate can then be further concentrated to at least 40% isoflavones by weight of dry matter by adjusting pH and temperature and extracting with solvents. The soy isoflavone concentrate products are then used in a liquid or dry beverage, food or nutritional products.

24 Claims, No Drawings

SOY ISOFLAVONE CONCENTRATE PROCESS AND PRODUCT

This application is a continuation-in-part of U.S. patent application Ser. No. 09/169,896, filed Oct. 12, 1998, now U.S. Pat. No. 6,228,993, and claims benefit of 60/062,046, filed Oct. 15, 1997, now abandoned.

FIELD OF THE INVENTION

A novel process for making an isoflavone concentrate product from soybeans which includes diluting solubles from alcohol-extracted hexane-defatted soybean flakes to about 10% to about 30% solids, separating undissolved solids from the diluted soy solubles, such that the separated solids have at least 4% isoflavones by weight of dry matter. That concentrate can then be further concentrated to at least 40% isoflavones by weight of dry matter by adjusting pH and temperature and extracting with solvents. The soy isoflavone concentrate products are then used in liquid or dry beverage, food or nutritional products.

BACKGROUND OF THE INVENTION

This invention relates to a process for making an isoflavone concentrate product from soybeans. Isoflavones are a unique class of phytoestrogens—plant hormones—that naturally occur in soybeans.

It is anticipated that consumer demand for soy isoflavones will continue to grow. Scientists have demonstrated that isoflavones have the ability to inhibit cancer cell growth, and some researchers believe that isoflavones may contribute to soy's ability to lower blood-cholesterol levels.

Research shows that soy isoflavones have a wide range of health benefits that include moderating normal symptoms associated with menopause and promoting bone and heart health. It appears that about 100 milligrams of isoflavones (expressed in the glucoside form) are necessary to deliver most of these health benefits. This is about the average amount consumed daily by Asian men and women who have a much lower incidence of heart disease, osteoporosis and uncomfortable menopausal symptoms compared to Western societies.

Some women's health problems during and after middle age are related to a changing hormonal state. Consuming soy isoflavones can help moderate the natural hormonal changes associated with several menopausal and postmenopausal symptoms.

Soy isoflavones are potent antioxidants capable of reducing the amount of LDL-cholesterol (bad cholesterol) that undergoes modification in the body. Entry of the modified LDL-cholesterol into the walls of blood vessels contributes to the formation of plaques. These plaques cause the blood vessels to lose their ability to function normally. Research in both animals and humans shows that ingesting soy isoflavones can help maintain normal blood vessel function.

Soy isoflavones are actively studied for their effects on maintaining and improving bone health. Women can lose up to 15% of their total bone mass in the early years following the onset of menopause. This loss can be quite detrimental, particularly to women who enter menopause with weaker bones. Emerging research shows that isoflavones appear to play a role in both preventing bone loss and increasing bone density.

The principal types of isoflavones found in soybeans are glucones (with sugars) and aglucones (without sugars). Glucones have the glucose molecule attached, and include genistin, daidzin and glycitin. Aglucones are isoflavones without the glucose molecule, and they include genistein, daidzein and glycitein. It is an object of this invention to produce products with the isoflavones genistein, daidzein and glycitein in similar proportions as those found naturally in soybeans when isoflavones are reported in the aglucone form.

The prior art teaches isolating genistin from hexane-extracted soybean flakes. Walter ("Genistin (an Isoflavone Glucoside) and Its Aglucone, Genistein, from Soybeans," *J. of Am. Chem. Soc.*, 63, 3273 (1941)) describes a method involving, among other steps, extracting the flakes with methanol, precipitating with acetone and recrystallizing with ethanol.

U.S. Pat. No. 5,141,746 (Fleury et al.) describes a method for preparing an impure extract of two specific isoflavones daidzin malonate and genistin malonate. Fleury describes a method involving, among other steps, mixing hexane-defatted ground soybeans with 80 percent (%) aqueous methanol, filtering and drying; adjusting pH multiple times with, among other chemicals, hydrochloric acid and sodium hydroxide, and extracting with an organic solvent, such as butanol.

U.S. Pat. No. 5,352,384 (Shen) describes making an aglucone enriched fiber. Shen describes solubilizing isoflavones from soy flour by, among other steps, forming a slurry with an extractant, such as sodium, potassium or calcium hydroxide, to adjust the pH to the proteins' isoelectric point of 6.7–9.7, and reacting the slurry with the enzyme β-glucosidase.

It is apparent that an efficient process for removing isoflavones from soybeans is needed. It also is apparent that a low-cost soy isoflavone concentrate (SIC) product is needed.

The invention uses the by-product soy solubles to SIC products. Soy solubles are recovered from alcohol-extracted hexane-defatted soybean flakes. These solubles, sometimes called soy "molasses", are desolventized, such that they contain less than 0.5% alcohol, and typically are evaporated to 60% solids.

It was discovered that soy solubles, on average, contain 3.31 milligrams per gram (mg/g) genistin on a wet basis and have a total isoflavone content (i.e., daidzin, glycitin, genistin, mal-daidzin, mal-genistin, daidzein, glycitein, genistein and some unidentified isoflavones) of 8.96 mg/g on a wet basis as determined by high performance liquid chromatography (HPLC). The genistin to daidzin ratio of soybeans is about 1 to 1 and that ratio in soy solubles was found to be about 1–1.5 to 1.

It was further discovered that if the soy solubles are diluted with water to form a slurry and the undissolved solids are removed from the slurry to form a wet "cake", the cake contains a significantly concentrated amount of isoflavones.

It was further discovered that if the soy solubles, which have about 20 mg/g isoflavones on a dry basis, are diluted with water to a certain percent solids and the undissolved solids are separated from the diluted solubles that the isoflavone content of the solubles can be concentrated by at least 2 times, or about 4% isoflavones by weight of dry matter.

It was further discovered that the 4% isoflavone material can then be further concentrated to at least 40% isoflavones by weight of dry matter by adjusting pH and temperature and extracting with solvents, like acetone and hexane.

It was further discovered that acetone extraction of the isoflavone material separated from the soy solubles also yields a by-product solution that is high in saponins, which are beginning to be recognized as having many useful nutritional and health benefits like soy isoflavones.

SUMMARY OF THE INVENTION

The invention comprises a novel process for manufacturing a novel soy isoflavone concentrate (SIC) product. The isoflavone content by weight of the SIC product is 8 to 11 times that of soy flour, which typically has about 0.6% by weight isoflavones. More particularly, the SIC product contains at least 4% by weight isoflavones, 20–60% protein, with it typically being at least one-third protein, and a relatively low amount of fiber, with it typically being less than 5% crude fiber and less than 20% dietary fiber. The 4% material can then be further concentrated to produce a SIC product having at least 40% by weight isoflavones, with such product typically being greater than 80% carbohydrates, less than about 5–10% protein, about one-third dietary fiber and less than 5–10% crude fiber. The SIC products are then used in liquid or dry beverage, food or nutritional products.

DETAILED DESCRIPTION OF THE INVENTION

The invention comprises a novel process for manufacturing a novel soy isoflavone concentrate (SIC) product. The isoflavone content by weight of the SIC product is 8 to 11 times that of soy flour, which typically has about 0.6% by weight isoflavones. More particularly, the SIC product contains at least 4% by weight isoflavones, 20–60% protein, with it typically being at least one-third protein, and a relatively low amount of fiber, with it typically being less than 5% crude fiber and less than 20% dietary fiber. The 4% material can then be further concentrated to produce a SIC product having at least 40% by weight isoflavones, with such product typically being greater than 80% carbohydrates, less than about 5–10% protein, about one-third dietary fiber and less than 5–10% crude fiber. The SIC products are then used in a liquid or dry beverage, food or nutritional product.

The steps of the subject invention for making the above-described 4% isoflavone concentrate material are: dehulling whole soybeans; flaking the dehulled soybeans; extracting soybean oil from the flaked soybeans with hexane, a solvent; desolventizing the defatted soybean flakes without high heating or toasting to produce "white" flakes; extracting the white flakes with aqueous alcohol; recovering solubles from the extraction; desolventizing (removing alcohol) from the soy solubles; diluting the soy solubles with water to form a slurry; separating the undissolved solids from the slurry to form a cake and drying the wet cake.

The steps of the subject invention for making the above-described 40% isoflavone concentrate material are: providing solubles from desolventized alcohol-extracted hexane-defatted soybean flakes; diluting said solubles with water to about 10–30% solids; separating undissolved solids from said diluted solubles; mixing said separated solids with acetone and sodium hydroxide, with said mixture having a pH of about 6.5–7; heating said mixture to about 55–60 degrees Celsius and holding said heated mixture for an effective period of time; separating a centrate from said mixture; cooling said centrate; decanting said acetone from said cooled centrate to form an acetone extract of said isoflavones; removing said acetone from said extract; raising the pH of said extract to about 10–10.5 with sodium hydroxide; heating said extract to about 50–60 degrees Celsius; lowering the pH of said extract to about 4.5–5 with hydrochloric acid; mixing said extract with hexane; heating said second mixture to about 50–60 degrees Celsius and stirring for an effective period of time; removing said hexane from said second mixture to form a second extract; separating solids from said second extract with chilling and drying said solids to form the product having about at least 40% isoflavones by weight.

The general procedure for extracting soybean oil from soybeans is well described in the prior art. E.g., "Extraction of Oil from Soybeans," *J. Am. Oil Chem. Soc.*, 58, 157 (1981) and "Solvent Extraction of Soybeans," *J. Am. Oil Chem. Soc.*, 55, 754 (1978).

An initial step in soybean oil extraction is the dehulling process in which the soybean hulls are removed from the whole soybeans. The soybeans are carefully cleaned prior to dehulling to remove foreign matter, so that product will not be contaminated by color bodies. Soybeans also are normally cracked into about 6 to 8 pieces prior to dehulling.

The hull typically accounts for about 8% of the weight of the whole soybean. The dehulled soybean is about 10% water, 40% protein, 20% fat, with the remainder mainly being carbohydrates, fiber and minerals.

The next step in soybean oil extraction involves the flaking process. Soybeans are conditioned prior to flaking by adjusting moisture and temperature to make the bean pieces sufficiently plastic. The conditioned bean pieces are passed through flaking rolls to form flakes about 0.01 to 0.012 inches (in.) thick.

The soybean flakes are defatted by contacting them with hexane to remove the soybean oil. Soybean oil is used in margarine, shortening and other food and products, and is a good source of lecithin, which has many useful applications as an emulsifier.

A detailed description of the general procedure for the alcohol process for manufacturing soy protein concentrate (SPC) is found in U.S. Pat. Nos. 3,365,440 (Circle et al.) and 5,097,017 (Konwinski). SPC has been described in commerce as a product containing not less than 70% protein (N×6.25). See A. K. Smith and S. J. Circle, Editors, "Soybeans: Chemistry and Technology, Volume I, Proteins," the AVI Publishing Co., 1973.

In the alcohol process, the hexane-defatted soybean flakes are desolventized—hexane is removed—without toasting to produce white flakes. This is different than conventional soybean oil hexane processes where the flakes are toasted and used for animal feed. Instead of being further processed into SPC, the white flakes can be ground to make soy flour.

The white flakes are extracted with 55–75%, typically 60%, by weight aqueous ethanol in a countercurrent (flake to solvent flow) extraction device—extractor. The alcohol to flake ratio is about 5 to 1.

The alcohol extraction removes carbohydrates, including oligosaccharides, from the white flakes, which thereby increases the protein content of the material. A typical sample of soy molasses from the SPC alcohol process was found to contain 7.80, 128.50, 19.45 and 86.79 milligrams/gram (mg/g) glucose, sucrose, raffinose and stachyose, respectively, on a wet basis. Soy molasses also typically contains 7–8% protein.

In the preferred embodiment of this invention, the diluting, separating, pasteurizing and drying steps to make the 4% isoflavone product are performed in a continuous process.

The soy solubles are diluted with water to form a slurry. Cold tap water is preferred source of water for the dilution.

In a preferred embodiment of this invention, the solubles are diluted to about 10% to about 30%, most preferred 18% solids. The slurry's pH being 5.5–6.

It also usually is necessary to provide some agitation or mixing to slurry the diluted solubles. One means for performing the mixing is a propeller-type agitator. The diluted soy solubles may be optionally cooled using a chiller.

The undissolved solids are removed from the slurry to form a wet cake. The undissolved solids could be removed by a number of physical separation means; however, centrifugation is the most efficient and effective means.

In the preferred embodiment of this invention, a scroll-type centrifuge is used to remove the undissolved solids from the slurry, such that wet cake is 25–30% solids and contains about 10–20% of the soy solubles' solids. In yet another embodiment of this invention, the separation can be performed with a disc type or tubular centrifuge.

Alternatively, the dilution and separation steps 8 and 9 could be described as water "washing" the soy solubles. These steps serve to concentrate the soy isoflavones from the solubles. In another embodiment of this invention, the washing process may be repeated one or more times in an effort to further concentrate the isoflavones, however, product yield (the quantity of SIC produced) would decrease.

In a preferred embodiment of this invention the wet cake is pasteurized prior to the drying step, so that the SIC will test negative for salmonella and have an acceptable microbial profile. One means for pasteurization is to hold the wet cake in a steam-jacketed kettle for 10 minutes at 160 degrees Fahrenheit (°F.).

The wet cake is dried to produce SIC useable as a nutritional supplement, or a food ingredient or product. The preferred means of drying is a vertical spray drier with a high pressure nozzle. To facilitate spray drying, the wet cake is diluted to less than 25% solids, most preferred 15%, prior to pasteurization.

A lot prepared by the above method had 6.9% isoflavones (66.7% genistein; 32.1% daidzein and 1.2% glycitein when isoflavones are reported in the aglucone form); 32.8% protein; 2.1% fat; 55.6% total carbohydrates; 4.4% moisture and 5.1% ash, with no heavy metals detected. When analyzed for isoflavones using standard HPLC methodology, the lot had 40.7 milligrams/gram (mg/g) genistin; 20.7 mg/g daidzin; 0.8 mg/g glycitin; 1 mg/g daidzein; 0.7 mg/g genistein and 0 glycitein.

Another lot prepared by the above method had 4.5% isoflavones (57.8% genistein; 37.4% daidzein and 4.6% glycitein when isoflavones are reported in the aglucone form); 30.2% protein; 1.3% fat; 59.5% total carbohydrates; 3.8% moisture and 5.2% ash, with no heavy metals detected. When analyzed for isoflavones using standard HPLC methodology, the lot had 23.7 milligrams/gram (mg/g) genistin; 14.3 mg/g daidzin; 2.0 mg/g glycitin; 1.6 mg/g daidzein; 0.04 mg/g genistein and 0 glycitein. These about 4% isoflavone concentrate products typically contain about 10% saponins by weight.

The spray-dried powdered SIC has many uses. For example, it can be tableted or used in drink mixes.

The spray-dried powdered SIC may be coated with commercial lecithin or other food-grade surfactants, such as mono-diglycerides, to improve water dispersibility and reduce clumping of the product. Such a coating-addition would be in the range of about 0.5%.

Prior to or after spray drying the wet cake, the cake can be further concentrated to at least 40% by weight isoflavones by adjusting pH and temperature and extracting with solvents.

The wet cake or slurried spray-dried cake is mixed with a solvent and its pH is adjusted to about 6–7, most preferred 6.4–6.8. Soy solubles or diluted soy solubles could also be suitable materials for this isoflavone extraction process.

Acetone is the preferred solvent. 50% sodium hydroxide is the preferred base for adjusting pH if necessary.

The ratio of starting material to the acetone/water mixture can vary. The efficiency of extraction using a ratio of starting material to acetone/water mixture of approximately 1 to 10 by mass is typically very high, often exceeding 90%.

The mixture is then extracted by heating to acetone reflux, 57–58 degrees Celsius. Alternatively, the extraction could be performed without heating if given sufficient time.

In addition to heating, it also preferred to hold the material for about 90 minutes to aid the extraction. It also preferred to then cool the heated material.

After extraction, a centrate is separated from the mixture. One means of separation is with a horizontal type centrifuge. Solids from the centrifugation may be dried with a pin dryer. The solids contain the majority of the protein in the about 4% isoflavone starting material.

After separation, it is desired to cool the centrate. One means for cooling the centrate is by passing it through a heat exchanger.

Saponins, another phytochemical, can then be removed from the centrate by decanting the solvent. The majority, at least about 60%, of the saponins in the 4% isoflavone starting material are in the solution. The isoflavones remain in the decanted solvent. It is preferred to cool and hold the centrate at less than 10 degrees Celsius prior to decanting to accumulate the saponins.

The saponins can be separated from the solution. One means of separation is with a disc type centrifuge.

The solvent, acetone in the preferred embodiment, is then removed from the decanted solvent. One means for removing the solvent is stripping it at ambient temperature to 90–95 degrees Celsius to form an extract. The recovered alcohol can then be re-used in the process.

The next steps in the process serve to saponify and remove lipids and certain emulsifying agents, like lecithin. This facilitates drying of the isoflavone concentrate.

The pH of the extract is then raised, most preferred 10–10.5. Again, sodium hydroxide is a suitable reagent for raising pH. It is then preferred to heat the pH raised extract to 60 degrees Celsius. These steps cleave glycerides from the lipids.

The pH of the extract is then further adjusted by lowering the pH, most preferred 4.5–5. Hydrochloric acid is a suitable reagent for lowering the pH. The chlorine binds with sodium in the extract to form sodium chloride.

An alkane is then used to perform a second extraction. Hexane is the preferred alkane. If necessary, water is added prior to adding the alkane. Free fatty acids are extracted by the hexane.

The alkane mixture is then heated to aid extraction, most preferred about 50 degrees Celsius. It also preferred to vigorously stir the mixture for about 30 minutes.

The mixture is then decanted by allowing it to settle. The decanted hexane and rag layers can then be distilled, so that the hexane may be re-used in the process.

The decanted water layer could then be dried. It is, however, preferred to chill the decanted water layer with precipitate to 5 degrees Celsius.

Wet solids are then separated with a disc type centrifuge. Secondary recovery of wet solids from the centrate of that centrifugation can be done with a horizontal type centrifuge to increase yield. The centrate from the centrifugation contains soluble carbohydrates from the starting material.

The wet solids are typically dried with a contact freeze drier. Prior to drying, the wet solids are sometimes blended or diluted with other isoflavone materials, such soy solubles or the above-described 4% material, to achieve a desired isoflavone content.

A lot prepared by the above method had 55.6% isoflavones (62.5% genistein; 34% daidzein and 3.5% glycitein when isoflavones are reported in the aglucone form); 5.4% protein; 1.1% fat; 87.2 total carbohydrates; 35.1% dietary fiber; 8.9% total sugars; 2.0% moisture and 4.3% ash. When analyzed for isoflavones using standard HPLC methodology, the lot had 278.9 milligrams/gram (mg/g) genistin; 150.4 mg/g daidzin; 15.9 mg/g glycitin; 2.9 mg/g daidzein; 2.6 mg/g genistein and 0 glycitein.

Another lot prepared by the above method had 49.3% isoflavones (72.7% genistein; 25.3% daidzein and 2.4% glycitein when isoflavones are reported in the aglucone form); 1.8% protein; 2.0% fat; 89.6% total carbohydrates; 2.4% moisture and 5.1% ash. When analyzed for isoflavones using standard HPLC methodology, the lot had 333.5 milligrams/gram (mg/g) genistin; 117.2 mg/g daidzin; 11.3 mg/g glycitin; 3.2 mg/g daidzein; 3.4 mg/g genistein and 0 glycitein. These isoflavone concentrates typically contain about 10–20% saponins by weight.

These and other aspects of the present invention may be more readily understood by reference to one or more of the following examples. These examples illustrate the practice of this invention.

EXAMPLE 1

Solubles with 53.5% solids and 11.6 milligrams/gram (mg/g) total isoflavones on a wet basis were recovered from alcohol-extracted hexane-defatted soybean flakes. The solids content of the solubles was adjusted to approximately 18%, and the resulting slurry was passed through a scroll-type centrifuge at a feed rate of 30 gallons per minute. The cake contained about 27% solids, and was diluted to about 18% solids. It was then pasteurized at 170 degrees Fahrenheit (°F.), and spray dried at a rate of about 400 pounds (lbs.) of dry solids per hour in a vertical spray dryer using pressure nozzles. The spray-dried product contained 6.1% total isoflavones.

EXAMPLE 2

Solubles with 55.9% solids were recovered from alcohol-extracted hexane-defatted white soybean flakes. 150 pounds (lbs.) of the solubles at 38 degrees Fahrenheit (°F.) were mixed with 303 lbs. of cold tap water with a propeller-type mixer to form a slurry of 453 lbs. of material with 17.72% solids at 63° F. The slurry was passed through a Sharples tubular bowl (Model AS-12) scroll-type centrifuge to form 23.35 lbs. of cake with 35.5% solids. The cake was freeze-dried to produce a product with a total isoflavone content of 82.44 milligrams/gram (mg/g).

EXAMPLE 3

1 kg of a dry soy soluble derived material having 4.8% isoflavones by weight (feedstock) was mixed with 2.35 kilograms (kg) of water and 9.45 kg of acetone. The pH of the mixture was adjusted to 6.4–6.8 by adding approximately 75 grams (g) of 50% sodium hydroxide (NaOH) over 30 minutes. The mixture was heated to 57–58 degrees Celsius with stirring and held at reflux for 90 minutes. 780 g of solids were separated with a Broadbent-Bird disc type centrifuge. The solids had less than 0.8% isoflavones after drying. The acetone was stripped from the centrate at atmospheric pressure to 95 degrees Celsius. The volume was reduced from 13.5 liters/kg starting material to 1.4–1.5 liters/kg feedstock. The acetone stripped aqueous slurry from six extractions was accumulated and refrigerated. The pH of the combined slurries was elevated to 10–10.5 by adding approximately 5 g of 50% NaOH solution per kg feedstock. The pH was lowered by adding approximately 12 g concentrated hydrochloric acid per kg feedstock. 280 g of hexane per liter of slurry were added, which equals 400 g (0.6 liters) hexane per kg feedstock. The mixture was vigorously agitated at 50 degrees Celsius for 30 minutes. The mixture was cooled to ambient temperature. The supernatant hexane layer was decanted, along with the rag and some of the aqueous phase above the settled solids, which was about 35% of the total volume. The bottom aqueous layer with precipitate was separated with a Bird decanting centrifuge. The blowdown from the centrifuge was sent to a double-cone dryer. The resulting final material was greater than 50% by weight isoflavones and greater than 80% of the isoflavones in the feedstock were recovered. The genistin-daidzin ratio of the resulting material was close to that of the feedstock.

EXAMPLE 4

950 pounds (lbs.) (430.9 kilograms (kg)) a dry soy soluble derived material having 5–6.5% isoflavones by weight (feedstock) is mixed with 268 gallons (gal.) (2233 lbs.) water (2.35 kg water/kg feedstock); 1362 gal. (8977 lbs.) acetone (9.45 kg acetone/kg feedstock) and 9 gal. 50% sodium hydroxide (NaOH) (75 grams/kg feedstock). The mixture is heated to 57–58 degrees Celsius with stirring and held at reflux for 90 minutes and then cooled to 60 degrees Celsius at 760 mm Hg. 1550 gal. of acetone water extract are removed with a Sharples horizontal type centrifuge. 1647 lbs. of wet solids from the centrifugation are dried with a pin dryer to make 7412 lbs. solids (88–94% extraction efficiency). The extract is cooled in a heat exchanger. Saponins are accumulated in a wash tank by holding at less than 10 degrees Celsius. The solvent is decanted. The saponins are 20 grams/kg feedstock. The saponins are further separated with a Bird disc type centrifuge. The decanted solvent is stripped of acetone at ambient to 90–95 degrees Celsius. The pH is raised to about 10–10.5 with 39–43 lbs. sodium hydroxide. The mixture is heated to 60 degrees Celsius. The pH is lowered to about 4.5–5 with 95–105 lbs. hydrochloric acid. 3.5 liters water/kg feedstock is added. 600 milliliters (400 grams) hexane/kg feedstock is added. The mixture is heated 50 degrees Celsius and stirred for 30 minutes. The mixture is allowed to settle and then is decanted. The water layer is chilled to 5 degrees Celsius and separated with a Bird disc type centrifuge. The wet solids are diluted/blended with feedstock, pasteurized and contact freeze dried to form a product having greater than 50% isoflavones by weight of dry matter. 75% of the isoflavones in the feedstock are recovered.

It will be understood that the claims are intended to cover all changes and modifications of the preferred embodiments of the invention herein chosen for the purpose of illustration which do not constitute a departure from the spirit and scope of the invention.

What is claimed is:

1. A process for concentrating isoflavones comprising:
   (a) providing an isoflavone material by separating undissolved solids from soy solubles, with said solids forming said material;

(b) mixing said material with a solvent and adjusting the pH to about 6–7;

(c) heating said mixture;

(d) decanting said solvent from said mixture to form a solvent extract of said isoflavones.

2. The process of claim 1 wherein said material is provided by diluting desolventized solubles to about 10–30% solids and separating said undissolved solids from said diluted solubles to form said material having about at least 4% isoflavones by weight of dry matter.

3. The process of claim 1 wherein said solvent of step (b) is acetone.

4. The process of claim 1 wherein said pH is 6.4–6.8.

5. The process of claim 1 wherein said heating is at 57–58 degrees Celsius.

6. The process of claim 1 further comprising cooling said mixture to about 50–60 degrees Celsius prior to said decanting step, with said decanting step producing a solid byproduct containing at least 60% by weight of the protein in said material.

7. The process of claim 3 further comprising (e) cooling said extract and (f) decanting said cooled extract.

8. The process of claim 7 further comprising: (g) removing said acetone from said decanted extract; (h) adjusting the pH of said acetone-stripped extract and heating; (i) adding an alkane to said extract and (j) removing said alkane.

9. The process of claim 8 further comprising heating and mixing prior to removing said alkane.

10. The process of claim 8 wherein step (h) is performed by raising the pH of said solution to about 10–10.5 with sodium hydroxide to saponify lipids and phospholipids in said material; heating and lowering the pH to about 4.5–5 with hydrochloric acid to release free fatty acids from said saponified lipids and phospholipids.

11. The process of claim 10 wherein the cooling in step (e) is at less than 10 degrees Celsius and the heating in step (h) is at about 50–60 degrees Celsius.

12. The process of claim 10 wherein said alkane is hexane and said removed hexane contains the majority of said free fatty acids.

13. The process of claim 9 wherein the mixing is for about 30 minutes.

14. The process of claim 8 further comprising drying said alkane removed extract to form a product having at least 40% isoflavones by weight.

15. The process of claim 14 further comprising chilling said alkane removed solution to about 5 degrees Celsius and separating solids to be dried in the drying step.

16. A liquid or dry beverage, food or nutritional product that uses the product of claim 15.

17. The process of claim 7 wherein said second decanting step (f) produces a solid byproduct primarily composed of phytochemicals in said material that are not said isoflavones.

18. An acetone-extracted soy isoflavone product, with said product having at least 40% isoflavones by weight of dry matter and a genistin to daidzin ratio of about 1.5–2.5 to 1.

19. The product of claim 18 wherein about 55–75% of said isoflavones are genistein; at least 20–40% of said isoflavones are daidzein and less than 5% of said isoflavones are glycitein when said isoflavones are reported in the aglucone form.

20. The product of claim 18 wherein said product is extracted from an isoflavone material aqueously separated from alcohol-extracted soy solubles, with said material having at least 4% isoflavones by weight of dry matter, said product and said material having a genistin to daidzin ratio of about 1.5–2 to 1 and said solubles having a genistin to daidzin ratio of about 1–1.5 to 1.

21. A liquid or dry beverage, food or nutritional product that uses the product of claim 18.

22. A process for concentrating isoflavones comprising:

(a) providing solubles from desolventized alcohol-extracted hexane-defatted soybean flakes;

(b) diluting said solubles with water to about 10–30% solids;

(c) separating undissolved solids from said diluted solubles;

(d) mixing said separated solids with acetone and adjusting the pH of said mixture to about 6–7;

(e) heating said mixture;

(f) decanting said acetone from said mixture to form an acetone extract of said isoflavones.

23. The process of claim 22 further comprising:

(g) removing said acetone from said extract;

(h) raising the pH, heating and lowering the pH of said extract;

(i) mixing said extract with hexane and heating said second mixture;

(j) removing said hexane from said second mixture to form a second extract;

(k) drying said second extract to form a product having at least 40% isoflavones by weight.

24. A liquid or dry beverage, food or nutritional product that uses the product of claim 23.

* * * * *